United States Patent
Dakka et al.

(10) Patent No.: US 7,812,196 B2
(45) Date of Patent: *Oct. 12, 2010

(54) PROCESS FOR PRODUCING PHENOL AND METHYL ETHYL KETONE

(75) Inventors: Jihad M. Dakka, Whitehouse Station, NJ (US); Edmund J. Mozeleski, Califon, NJ (US); Jane C. Cheng, Bridgewater, NJ (US); Francisco M. Benitez, Houston, TX (US); Jon E. Stanat, Houston, TX (US); John S. Buchanan, Lambertville, NJ (US)

(73) Assignee: ExxonMobil Chemical Patents Inc., Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 12/162,959

(22) PCT Filed: Feb. 8, 2007

(86) PCT No.: PCT/EP2007/001210

§ 371 (c)(1),
(2), (4) Date: Nov. 10, 2008

(87) PCT Pub. No.: WO2007/093362

PCT Pub. Date: Aug. 23, 2007

(65) Prior Publication Data

US 2009/0306433 A1 Dec. 10, 2009

Related U.S. Application Data

(60) Provisional application No. 60/773,147, filed on Feb. 14, 2006.

(51) Int. Cl.
*C07C 45/53* (2006.01)
*C07C 37/08* (2006.01)

(52) U.S. Cl. .......... 568/385; 568/768; 568/798
(58) Field of Classification Search .......... 568/385, 568/768, 798
See application file for complete search history.

(56) References Cited

U.S. PATENT DOCUMENTS

| 4,891,458 | A | | 1/1990 | Innes et al. .......... 585/323 |
|---|---|---|---|---|
| 4,992,606 | A | | 2/1991 | Kushnerick et al. .......... 525/467 |
| 5,183,945 | A | * | 2/1993 | Stibrany et al. .......... 568/574 |
| 5,298,667 | A | * | 3/1994 | Iwanaga et al. .......... 568/385 |
| 5,371,310 | A | | 12/1994 | Bennett et al. .......... 585/467 |
| 5,557,024 | A | | 9/1996 | Cheng et al. .......... 585/467 |
| 5,779,882 | A | | 7/1998 | Chester et al. .......... 208/120 |
| 5,922,920 | A | * | 7/1999 | Bond et al. .......... 568/342 |
| 6,717,025 | B1 | * | 4/2004 | Risch et al. .......... 585/804 |
| 6,720,462 | B2 | * | 4/2004 | Duda et al. .......... 568/768 |
| 2008/0086018 | A1 | | 4/2008 | Cheng et al. .......... 568/365 |

FOREIGN PATENT DOCUMENTS

| EP | 0 548 986 | 6/1993 |
|---|---|---|
| EP | 0 719 750 | 7/1996 |

OTHER PUBLICATIONS

Yen, "Phenool," *Process Economics Program Report No. 22B: Phenol Supplement B*, Stanford Research Institute, pp. 113-121, 261 and 263 (1977).

* cited by examiner

*Primary Examiner*—Sikarl A Witherspoon (57) ABSTRACT

A process for producing phenol and methyl ethyl ketone comprises contacting benzene and a $C_4$ olefin under alkylation conditions and in the presence of an alkylation catalyst to produce an alkylation effluent comprising sec-butylbenzene and $C_8+$ olefins. The alkylation effluent is then treated to reduce the amount of said $C_8+$ olefins and produce a treated effluent, whereafter the sec-butylbenzene in the treated effluent is oxidized to produce a hydroperoxide and the hydroperoxide is cleaved to produce phenol and methyl ethyl ketone.

20 Claims, 2 Drawing Sheets

Figure 3. Comparison of Oxidation Activity with Various Treatments

US 7,812,196 B2

PROCESS FOR PRODUCING PHENOL AND METHYL ETHYL KETONE

CROSS-REFERENCE TO RELATED APPLICATIONS

This application is a National Stage Application of International Application No. PCT/EP2007/001210 filed Feb. 8, 2007, which claims priority from U.S. Ser. No. 60/773,147 filed Feb. 14, 2006, both of which are incorporated herein by reference.

FIELD

The present invention relates to a process for co-producing phenol and methyl ethyl ketone.

BACKGROUND

Phenol and methyl ethyl ketone are important products in the chemical industry. For example, phenol is useful in the production of phenolic resins, bisphenol A, ε-caprolactam, adipic acid, alkyl phenols, and plasticizers, whereas methyl ethyl ketone can be used as a lacquer, a solvent and for dewaxing of lubricating oils.

The most common route for the production of methyl ethyl ketone is by dehydrogenation of sec-butyl alcohol (SBA), with the alcohol being produced by the acid-catalyzed hydration of butenes. For example, commercial scale SBA manufacture by reaction of butylene with sulfuric acid has been accomplished for many years via gas/liquid extraction.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone. However, the world demand for phenol is growing more rapidly than that for acetone. In addition, the cost of propylene relative to that for butenes is likely to increase, due to a developing shortage of propylene. Thus, a process that uses butenes instead of propylene as feed and co-produces methyl ethyl ketone rather than acetone may be an attractive alternative route to the production of phenol.

It is known that phenol and methyl ethyl ketone can be co-produced by a variation of the Hock process in which sec-butylbenzene is oxidized to obtain sec-butylbenzene hydroperoxide and the peroxide decomposed to the desired phenol and methyl ethyl ketone. An overview of such a process is described in pages 113-121, 261, and 263 of Process Economics Report No. 22B entitled "Phenol", published by the Stanford Research Institute in December 1977.

Sec-butylbenzene can be produced by alkylating benzene with n-butenes over an acid catalyst. The chemistry is very similar to ethylbenzene and cumene production. However, as the carbon number of the alkylating agent increases, the number of product isomers also increases. For example, ethylbenzene has one isomer, propylbenzene has two isomers (cumene and n-propylbenzene), and butylbenzene has four isomers (n-, iso-, sec-, and t-butylbenzene). For sec-butylbenzene production, it is important to minimize n-, iso-, t-butylbenzene, and phenylbutenes by-product formation. These by-products, especially iso-butylbenzene, have boiling points very close to sec-butylbenzene and hence are difficult to separate from sec-butylbenzene by distillation (see table below).

| Butylbenzene | Boiling Point, ° C. |
|---|---|
| t-Butylbenzene | 169 |
| i-Butylbenzene | 171 |
| s-Butylbenzene | 173 |
| n-Butylbenzene | 183 |

Moreover, isobutylbenzene and tert-butylbenzene are known to be inhibitors to the oxidation of sec-butylbenzene to the corresponding hydroperoxide, a necessary next step for the production of methyl ethyl ketone and phenol. Thus, for commercial production, it is critical to maximize the sec-butylbenzene selectivity of the alkylation process.

In addition, although sec-butylbenzene production can be maximized by using a pure n-butene feed, it is desirable to employ more economical butene feeds, such as Raffinate-2. A typical Raffinate-2 contains 0-1% butadiene and 0-5% isobutene. With this increased isobutene in the feed, a higher by-product make is expected, which further increases the importance of the sec-butylbenzene selectivity of the process.

U.S. Pat. No. 4,891,458 discloses a process for the alkylation of an aromatic hydrocarbon which comprises contacting a stoichiometric excess of the aromatic hydrocarbon with a $C_2$ to $C_4$ olefin under at least partial liquid phase conditions and in the presence of a catalyst comprising zeolite beta. In addition, it is known from, for example, U.S. Pat. No. 4,992,606 that MCM-22 is an effective catalyst for alkylation of aromatic compounds, such as benzene, with alkylating agents, such as olefins, having from 1 to 5 carbon atoms over a wide range of temperatures from about 0° C. to about 500° C., preferably from about 50° C. and about 250° C. Similar disclosures are contained in U.S. Pat. Nos. 5,371,310 and 5,557,024 but where the zeolites are MCM-49 and MCM-56 respectively.

In our International Application No. PCT/EP2005/008557, filed Aug. 5, 2005, we have described an integrated process for producing phenol and methyl ethyl ketone, the process comprising (a) contacting a feed comprising benzene and a $C_4$ alkylating agent under alkylation conditions with a catalyst comprising zeolite beta or an MCM-22 family zeolite to produce an alkylation effluent comprising sec-butylbenzene; (b) oxidizing the sec-butylbenzene to produce a hydroperoxide; and then (c) cleaving the hydroperoxide to produce phenol and methyl ethyl ketone. The $C_4$ alkylating agent can be a mixed butene feed, such as Raffinate-1 or Raffinate-2.

According to the present invention, it has now been found that the oxidation of sec-butylbenzene is sensitive not only isobutylbenzene and tert-butylbenzene in the feed, but also to higher ($C_8$+) olefins that tend to be produced as a result of the competing oligomerization reactions that occur when butene is contacted with an acid catalyst under alkylation conditions. It has also been found that the production of these olefin oligomers is increased when a mixed butene feed, such as Raffinate-1 or Raffinate-2, is used as the $C_4$ alkylating agent.

SUMMARY

In one aspect, the present invention resides in a process for producing phenol and methyl ethyl ketone, the process comprising:

(a) contacting benzene and a $C_4$ olefin under alkylation conditions and in the presence of an alkylation catalyst to produce an alkylation effluent comprising sec-butylbenzene and $C_8$+ olefins;

(b) treating said effluent to reduce the amount of said $C_8+$ olefins and produce a treated effluent;

(c) oxidizing the sec-butylbenzene in said treated effluent to produce a hydroperoxide; and (d) cleaving the hydroperoxide from (c) to produce phenol and methyl ethyl ketone.

Preferably, the treating (b) includes a chemical treatment, such as olefin oligomerization, selective reduction, selective oxidation, esterification, and the addition of heteroatoms to olefins, or a combination thereof.

In one embodiment, the catalyst comprises at least one molecular sieve of the MCM-22 family. Conveniently, the molecular sieve of the MCM-22 family has an X-ray diffraction pattern including d-spacing maxima at 12.4±0.25, 6.9±0.15, 3.57±0.07 and 3.42±0.07 Angstrom. Conveniently, the molecular sieve is selected from MCM-22, PSH-3, SSZ-25, ERB-1, ITQ-1, ITQ-2, MCM-36, MCM-49, MCM-56, UZM-8, and mixtures thereof. Preferably, the molecular sieve is selected from MCM-22, MCM-49, MCM-56 and isotypes thereof.

Preferably, the $C_4$ olefin comprises a linear butene, for example 1-butene and/or 2-butene. In one embodiment, said linear butene is contained in a mixed $C_4$ stream which is subjected to at least one of sulfur removal, nitrogen removal, oxygenate removal, butadiene removal and isobutene removal prior to the contacting (a). Conveniently, said mixed $C_4$ stream is a Raffinate-1 or a Raffinate-2 stream.

Conveniently, said alkylation conditions also include a temperature of from about 60° C. to about 260° C., a pressure of 7000 kPa or less, a feed weight hourly space velocity (WHSV) based on $C_4$ alkylating agent of from about 0.1 to 50 $hr^{-1}$, and molar ratio of benzene to butene from about 1 to about 50, preferably about 2 to about 10.

In one embodiment, said contacting (a) is conducted under at least partial liquid phase conditions.

In one embodiment, said alkylation effluent produced in (a) comprises polybutylbenzenes and the process further comprises contacting said polybutylbenzenes with benzene in the presence of a transalkylation catalyst to produce sec-butylbenzene. Conveniently, the transalkylation catalyst comprises a molecular sieve selected from zeolite beta, mordenite, USY, MCM-22, PSH-3, SSZ-25, ERB-1, ITQ-1, ITQ-2, MCM-36, MCM-49, MCM-56, UZM-8, and mixtures thereof.

Conveniently, the oxidizing (b) is conducted in the presence of a catalyst, such as a catalyst selected from (i) an oxo(hydroxo) bridged tetranuclear metal complex comprising manganese, (ii) an oxo(hydroxo) bridged tetranuclear metal complex having a mixed metal core, one metal of the core being a divalent metal selected from Zn, Cu, Fe, Co, Ni, Mn and mixtures thereof and another metal being a trivalent metal selected from In, Fe, Mn, Ga, Al and mixtures thereof, (iii) an N-hydroxy substituted cyclic imide either alone or in the presence of a free radical initiator, and (iv) N,N',N"-trihydroxyisocyanuric acid either alone or in the presence of a free radical initiator. In one embodiment, the oxidization catalyst is a heterogeneous catalyst.

Conveniently, the oxidizing (b) is conducted at a temperature of about 70° C. to about 200° C. and a pressure of about 0.5 to about 20 atmospheres (50 to 2000 kPa). Conveniently, the cleaving (c) is conducted in the presence of a catalyst. The catalyst can be a homogeneous or heterogeneous catalyst. In one embodiment, the catalyst is a homogeneous catalyst, such as sulfuric acid.

Conveniently, the cleaving (c) is conducted at a temperature of about 40° C. to about 120° C., a pressure of about 100 to about 2500 kPa, and a liquid hourly space velocity (LHSV) based on the hydroperoxide of about 0.1 to about 100 $hr^{-1}$.

In a further aspect, the invention resides in a hydrocarbon composition boiling within 5° C. of sec-butylbenzene and comprising at least 95 wt % sec-butylbenzene and 20 to 1000 ppm wt, preferably 50 to 500 ppm wt, of butene oligomers. Preferably, said composition comprises less than 0.5 wt % of isobutylbenzene and tert-butylbenzene.

As used herein the term $C_8+$ olefin means any olefin containing 8 or more carbon atoms.

DETAILED DESCRIPTION OF THE EMBODIMENTS

The present invention is directed to a process for producing sec-butylbenzene by alkylating benzene with a $C_4$ alkylating agent, such as a linear butene, and then converting the sec-butylbenzene to phenol and methyl ethyl ketone. The conversion involves initially oxidizing the sec-butylbenzene to produce the corresponding hydroperoxide and then cleaving the resulting hydroperoxide to produce the desired phenol and methyl ethyl ketone.

In particular, the invention is based on the discovery that the oxidation step to convert the sec-butylbenzene to the corresponding hydroperoxide is highly sensitive to presence of butene oligomers in the alkylation effluent. Moreover, certain butene oligomers, particularly certain $C_{12}$ oligomers, have boiling points very close to that of sec-butylbenzene and hence can not be readily separated from alkylation effluent by distillation. Thus the present invention seeks to obviate or reduce this problem by subjecting the alkylation effluent to a treatment, preferably a chemical treatment, to reduce the level of butene oligomers in the effluent, typically to less than 1 wt %, preferably less than 0.7 wt %, and most preferably less than 0.5 wt %.

Benzene Alkylation

The benzene employed in the alkylation step to produce sec-butylbenzene can be any commercially available benzene feed, but preferably the benzene has a purity level of at least 99 wt %.

The alkylating agent can be any olefin, particularly any monoolefin, having 4 carbon atoms and preferably is a linear butene, such as butene-1 and/or butene-2. The alkylating agent can also be an olefinic $C_4$ hydrocarbon mixture such as can be obtained by steam cracking of ethane, propane, butane, LPG and light naphthas, catalytic cracking of naphthas and other refinery feedstocks and by conversion of oxygenates, such as methanol, to lower olefins.

For example, the following $C_4$ hydrocarbon mixtures are generally available in any refinery employing steam cracking to produce olefins; a crude steam cracked butene stream, Raffinate-1 (the product of remaining after solvent extraction or hydrogenation to remove butadiene from the crude steam cracked butene stream) and Raffinate-2 (the product remaining after removal of butadiene and isobutene from the crude steam cracked butene stream). Generally, these streams have compositions within the weight ranges indicated in Table A below.

TABLE A

| Component | Crude $C_4$ stream | Raffinate 1 | | Raffinate 2 | |
|---|---|---|---|---|---|
| | | Solvent Extraction | Hydrogenation | Solvent Extraction | Hydrogenation |
| Butadiene | 30-85% | 0-2% | 0-2% | 0-1% | 0-1% |
| C4acetylenes | 0-15% | 0-0.5% | 0-0.5% | 0-0.5% | 0-0.5% |
| Butene-1 | 1-30% | 20-50% | 50-95% | 25-75% | 75-95% |
| Butene-2 | 1-15% | 10-30% | 0-20% | 15-40% | 0-20% |
| Isobutene | 0-30% | 0-55% | 0-35% | 0-5% | 0-5% |
| N-butane | 0-10% | 0-55% | 0-10% | 0-55% | 0-10% |
| Iso-butane | 0-1% | 0-1% | 0-1% | 0-2% | 0-2% |

Other refinery mixed $C_4$ streams, such as those obtained by catalytic cracking of naphthas and other refinery feedstocks, typically have the following composition:

| | |
|---|---|
| Propylene | 0-2 wt % |
| Propane | 0-2 wt % |
| Butadiene | 0-5 wt % |
| Butene-1 | 5-20 wt % |
| Butene-2 | 10-50 wt % |
| Isobutene | 5-25 wt % |
| Iso-butane | 10-45 wt % |
| N-butane | 5-25 wt % |

$C_4$ hydrocarbon fractions obtained from the conversion of oxygenates, such as methanol, to lower olefins more typically have the following composition:

| | |
|---|---|
| Propylene | 0-1 wt % |
| Propane | 0-0.5 wt % |
| Butadiene | 0-1 wt % |
| Butene-1 | 10-40 wt % |
| Butene-2 | 50-85 wt % |
| Isobutene | 0-10 wt % |
| N- + iso-butane | 0-10 wt % |

Any one or any mixture of the above $C_4$ hydrocarbon mixtures can be used in the process of the invention. In addition to linear butenes and butanes, these mixtures typically contain components, such as isobutene and butadiene, which can be deleterious to the process of the invention. For example, the normal alkylation products of isobutene with benzene are tert-butylbenzene and iso-butylbenzene which, as previously stated, act as inhibitors to the subsequent oxidation step. Thus, prior to the alkylation step, these mixtures preferably are subjected to butadiene removal and isobutene removal. For example, isobutene can be removed by selective dimerization or reaction with methanol to produce MTBE, whereas butadiene can be removed by extraction or selective hydrogenation to butene-1.

In addition to other hydrocarbon components, commercial $C_4$ hydrocarbon mixtures typically contain other impurities which could be detrimental to the alkylation process. For example, refinery $C_4$ hydrocarbon streams typically contain nitrogen and sulfur impurities, whereas $C_4$ hydrocarbon streams obtained by oxygenate conversion process typically contain unreacted oxygenates and water. Thus, prior to the alkylation step, these mixtures may also be subjected to one or more of sulfur removal, nitrogen removal and oxygenate removal, in addition to butadiene removal and isobutene removal. Removal of sulfur, nitrogen, oxygenate impurities is conveniently effected by one or a combination of caustic treatment, water washing, distillation, adsorption using molecular sieves and/or membrane separation. Water is also typically removed by adsorption.

Although not preferred, it is also possible to employ a mixture of a $C_4$ alkylating agent, as described above, and $C_3$ alkylating agent, such as propylene, as the alkylating agent in the alkylation step of the invention so that the alkylation step produces a mixture of cumene and sec-butylbenzene. The resultant mixture can then be processed through oxidation and cleavage, to make a mixture of acetone and MEK, along with phenol, preferably where the molar ratio of acetone to phenol is 0.5:1, to match the demand of bisphenol-A production.

Conveniently, the total feed to the alkylation step of the present invention contains less than 1000 ppm, such as less than 500 ppm, for example less than 100 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen.

The alkylation catalyst used in the present process is a crystalline molecular sieve of the MCM-22 family. The term "MCM-22 family material" (or "material of the MCM-22 family" or "molecular sieve of the MCM-22 family" or "MCM-22 family zeolite"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof, and molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as the incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Molecular sieves of the MCM-22 family are preferred as the alkylation catalyst since they have been found to be highly selective to the production of sec-butylbenzene, as compared with the other butylbenzene isomers. Preferably, the molecular sieve is selected from MCM-22, MCM-49, MCM-56 and isotypes of MCM-22, MCM-49 and MCM-56, such as ITQ-2.

The alkylation catalyst can include the molecular sieve in unbound or self-bound form or, alternatively, the molecular sieve can be combined in a conventional manner with an oxide binder, such as alumina, such that the final alkylation catalyst contains between 2 and 80 wt % sieve.

The alkylation process is conducted such that the organic reactants, i.e., the alkylatable aromatic compound and the alkylating agent, are brought into contact with the alkylation catalyst in a suitable reaction zone such as, for example, in a flow reactor containing a fixed bed of the catalyst composition or in a catalytic distillation reactor, under effective alkylation conditions. Typically, the alkylation conditions include a temperature of from about 60° C. to about 260° C., for example between about 100° C. and about 200° C., a pressure of 7000 kPa or less, for example from about 1000 to about 3500 kPa, a weight hourly space velocity (WHSV) based on $C_4$ alkylating agent of between about 0.1 and about 50 $hr^{-1}$, for example between about 1 and about 10 $hr^{-1}$ and a molar ratio of benzene to alkylating agent is from about 1:1 to about 50:1, for example from about 2:1 to about 10:1, preferably from about 4:1 to about 9:1. Preferably, the alkylating agent is introduced to the reaction in stages, for example by providing the alkylation catalyst in a plurality of reaction zones connected in series and dividing the alkylating agent into a plurality of equal or different aliquot portions, each of which is fed to a different reaction zone. Most or all of the benzene is typically fed to the first reaction zone.

The reactants can be in either the vapor phase or partially or completely in the liquid phase or under supercritical conditions and can be neat, i.e., free from intentional admixture or dilution with other material, or they can be brought into contact with the zeolite catalyst composition with the aid of carrier gases or diluents such as, for example, hydrogen or nitrogen. Preferably, the reactants are at least partially in the liquid phase Using the catalyst and alkylation conditions described above, it is found that the alkylation step of the process of the invention is highly selective to sec-butylbenzene. However, the effluent from the alkylation reaction will normally contain some polyalkylated oligomerization products and, as will be discussed below, certain butene oligomers, in addition to unreacted benzene and the desired monoalkylated species. The unreacted benzene is normally recovered by distillation and recycled to the alkylation reactor. The bottoms from the benzene distillation are further distilled to separate monoalkylated product from any polyalkylated products and other heavies. Depending on the amount of polyalkylated products present in the alkylation reaction effluent, it may be desirable to transalkylate the polyalkylated products with additional benzene to maximize the production of the desired monoalkylated species.

Transalkylation with additional benzene is typically effected in a transalkylation reactor, separate from the alkylation reactor, over a suitable transalkylation catalyst, such as a molecular sieve of the MCM-22 family, zeolite beta, MCM-68 (see U.S. Pat. No. 6,014,018), zeolite Y and mordenite. Molecular sieves of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO 97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. The transalkylation reaction is typically conducted under at least partial liquid phase conditions, which suitably include a temperature of 100 to 300° C., a pressure of 1000 to 7000 kPa, a weight hourly space velocity of 1 to 50 $hr^{-1}$ on total feed, and a benzene/polyalkylated benzene weight ratio of 1 to 10.

Removal of Butene Oligomers

As stated above, the effluent from the alkylation reaction will normally contain butene oligomers, which have now been found to inhibit subsequent oxidation of the sec-butylbenzene to the corresponding hydroperoxide. Moreover, although distillation is effective to remove some of these impurities, certain butene oligomers, particularly the $C_{12}$ olefins, tend to boil at or near the same temperature as sec-butylbenzene and hence cannot be readily removed by distillation. Thus the present process employs an additional treatment process, particularly a chemical treatment process, to reduce the level of butene oligomers in the alkylation effluent, typically to less than 1 wt %, preferably less than 0.7 wt %, and most preferably less than 0.5 wt %.

One suitable chemical treatment to reduce the oligomer level in the alkylation effluent involves contacting the effluent with an acid, such as a mineral acid or a solid acid with optional water, at a temperature of about 0 to about 300° C. to convert the oligomers to alcohols or esters (e.g. esters of sulfuric acid). After neutralization of the excess acid and, if necessary washing, drying, and distillation, the effluent can be fed to the oxidation step.

Another suitable chemical treatment to reduce the oligomer level in the alkylation effluent involves contacting the effluent with hydrogen in the presence of a catalyst, such as a noble metal heterogenous catalyst, under conditions effective to saturate the oligomers. Suitable conditions include a temperature of about 0 to about 200° C., a pressure of about 100 to about 1000 kPa and a hydrogen to hydrocarbon mole ratio of about 0.001 to about 10.

A further suitable chemical treatment to reduce the oligomer level in the alkylation effluent involves etherification, in which the effluent is contacted with an alcohol, such as methanol, at a temperature of about 20 to about 300° C.

A combination of the above treatment processes, such as combination of acid treatment and hydrogenation, can be used to reduce the level of butene oligomers in the alkylation effluent to the desired level.

By virtue of the alkylation and treatment processes described above, the invention provides a hydrocarbon composition boiling within 5° C. of sec-butylbenzene and comprising at least 95 wt % sec-butylbenzene and 20 to 1000 ppm wt, preferably 50 to 500 ppm wt, of butene oligomers. Preferably, said composition comprises less than 0.5 wt % of isobutylbenzene and tert-butylbenzene.

Sec-Butylbenzene Oxidation

In order to convert the sec-butylbenzene into phenol and methyl ethyl ketone, the sec-butylbenzene is initially oxidized to the corresponding hydroperoxide. This is accomplished by introducing an oxygen-containing gas, such as air, into a liquid phase containing the sec-butylbenzene. Unlike cumene, atmospheric air oxidation of sec-butylbenzene in the absence of a catalyst is very difficult to achieve. For example, at 110° C. and at atmospheric pressure, sec-butylbenzene is not oxidized, while cumene oxidizes very well under the same conditions. At higher temperature, the rate of atmospheric air oxidation of sec-butylbenzene improves; however, higher temperatures also produce significant levels of undesired by-products.

Improvements in the reaction rate and selectivity can be achieved by performing sec-butylbenzene oxidation in the presence of a catalyst. Suitable sec-butylbenzene catalysts include a water-soluble chelate compound in which multidentate ligands are coordinated to at least one metal from cobalt, nickel, manganese, copper, and iron. (See U.S. Pat. No. 4,013,725). More preferably, a heterogeneous catalyst is used. Suitable heterogeneous catalysts are described in U.S. Pat. No. 5,183,945, wherein the catalyst is an oxo(hydroxo) bridged tetranuclear manganese complex and in U.S. Pat. No. 5,922,920, wherein the catalyst comprises an oxo(hydroxo) bridged tetranuclear metal complex having a mixed metal core, one metal of the core being a divalent metal selected from Zn, Cu, Fe, Co, Ni, Mn and mixtures thereof and another metal being a trivalent metal selected from In, Fe, Mn, Ga, Al and mixtures thereof. The entire disclosures of said U.S. patents are incorporated herein by reference.

Other suitable catalysts for the sec-butylbenzene oxidation step are the N-hydroxy substituted cyclic imides described in U.S. Pat. No. 6,720,462 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide. Preferably, the catalyst is N-hydroxyphthalimide. Another suitable catalyst is N,N',N"-thihydroxyisocyanuric acid.

These materials can be used either alone or in the presence of a free radical initiator and can be used as liquid-phase, homogeneous catalysts or can be supported on a solid carrier to provide a heterogeneous catalyst.

Suitable conditions for the sec-butylbenzene oxidation step include a temperature between about 70° C. and about 200° C., such as about 90° C. to about 130° C., and a pressure of about 0.5 to about 20 atmospheres (50 to 2000 kPa). A basic buffering agent may be added to react with acidic by-products that may form during the oxidation. In addition, an aqueous phase may be introduced, which can help dissolve basic compounds, such as sodium carbonate. The per-pass conversion in the oxidation step is preferably kept below 50%, to minimize the formation of byproducts. The oxidation reaction is conveniently conducted in a catalytic distillation unit and the sec-butylbenzene hydroperoxide produced may be concentrated by distilling off the unreacted sec-butylbenzene prior to the cleavage step.

Hydroperoxide Cleavage

The final step in the conversion of the sec-butylbenzene into phenol and methyl ethyl ketone involves cleavage of the sec-butylbenzene hydroperoxide, which is conveniently effected by contacting the hydroperoxide with a catalyst in the liquid phase at a temperature of about 20° C. to about 150° C., such as about 40° C. to about 120° C., a pressure of about 50 to about 2500 kPa, such as about 100 to about 1000 kPa and a liquid hourly space velocity (LHSV) based on the hydroperoxide of about 0.1 to about 100 $hr^{-1}$, preferably about 1 to about 50 $hr^{-1}$. The sec-butylbenzene hydroperoxide is preferably diluted in an organic solvent inert to the cleavage reaction, such as methyl ethyl ketone, phenol or sec-butylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid A suitable heterogeneous catalyst for use in the cleavage of sec-butylbenzene hydroperoxide includes a smectite clay, such as an acidic montmorillonite silica-alumina clay, as described in U.S. Pat. No. 4,870,217, the entire disclosure of which is incorporated herein by reference.

The following Examples are given for illustrative purposes and do not limit the scope of the invention.

Example 1

Sec-Butylbenzene Production Using MCM-22 Catalyst and 2-Butene Feed

A 1.0 gram sample of MCM-22 catalyst (65% MCM-22/35% alumina binder) was used for the alkylation of benzene with 2-butene. The catalyst was in the form of a 1.6 mm (1/16") diameter cylindrical extrudate, chopped to 1/16" length, and was diluted with sand to 3 cc and loaded into an isothermal, down-flow, fixed-bed, tubular reactor having an outside diameter of 4.76 mm (3/16"). The catalyst was dried at 150° C. and 1 atm with 100 cc/min flowing nitrogen for 2 hours. The nitrogen was turned off and benzene was fed to the reactor at 60 cc/hr until reactor pressure reached the desired 300 psig (2170 kPa). Benzene flow was then reduced to 7.63 cc/hr (6.67 WHSV) and a butene feed (57.1% cis-butene, 37.8% trans-butene, 2.5% n-butane, 0.8% isobutene and 1-butene, and 1.8% others) was introduced from a syringe pump at 2.57 cc/hr (1.6 WHSV). Feed benzene/butene molar ratio was maintained at 3:1 for the entire run and the reactor temperature was adjusted to 160° C. Liquid products were collected at reactor conditions of 160° C. and 300 psig (2170 kPa) in a cold-trap and analyzed off line. 2-Butene conversion was determined by measuring unreacted 2-butene relative to feed 2-butene. The catalyst was on stream for 4 days at 1.6 WHSV of butene with 97% 2-butene conversion, 2 days at 4.8 WHSV with 95% conversion, then 1 day at 7.2 WHSV with 86% conversion, and followed by 4 days again at 1.6 WHSV with 97% conversion. Representative data are shown in Table 1.

TABLE 1

| sec-Butylbenzene Production with MCM-22 and 2-Butene Feed | | | | |
|---|---|---|---|---|
| Days on Stream | 3.8 | 5.9 | 7.1 | 10.8 |
| Butene WHSV, $h^{-1}$ | 1.6 | 4.8 | 7.2 | 1.6 |
| 2-Butene Conv, % | 97.7 | 95.3 | 86.0 | 97.2 |
| Product Selectivity, wt % | | | | |
| Iso-Butane | 0.010 | 0.001 | 0.004 | 0.008 |
| Iso-Butene & 1-Butene | 0.000 | 0.020 | 0.355 | 0.000 |
| $C_5$-$C_7$ | 0.227 | 0.105 | 0.132 | 0.120 |
| $C_8$ and $C_{12}$ (butene oligomers) | 0.812 | 1.753 | 2.556 | 1.910 |
| Cumene | 0.077 | 0.050 | 0.031 | 0.059 |
| t-Butylbenzene | 0.158 | 0.060 | 0.026 | 0.103 |
| iso-Butylbenzene* | 0.000 | 0.000 | 0.000 | 0.000 |
| sec-Butylbenzene | 89.185 | 90.983 | 90.490 | 91.553 |
| n-Butylbenzene | 0.024 | 0.031 | 0.030 | 0.025 |
| Di-butylbenzene | 8.012 | 6.589 | 5.982 | 5.791 |
| Tri-butylbenzene | 1.239 | 0.420 | 0.392 | 0.417 |
| Heavies | 0.256 | 0.008 | 0.003 | 0.013 |
| Sum | 100.0 | 100.0 | 100.0 | 100.0 |
| Butylbenzene Composition, % | | | | |
| t-Butylbenzene | 0.177 | 0.065 | 0.029 | 0.112 |
| iso-Butylbenzene* | 0.000 | 0.000 | 0.000 | 0.000 |
| sec-Butylbenzene | 99.796 | 99.900 | 99.938 | 99.860 |
| n-Butylbenzene | 0.027 | 0.034 | 0.033 | 0.028 |
| Sum | 100.0 | 100.0 | 100.0 | 100.0 |

All samples collected at 160° C., 300 psig, and 3:1 benzene/butene molar ratio.
*iso-Butylbenzene less than 0.5% in total butylbenzene not detectable with GC used.

Example 2

Sec-Butylbenzene Production Using MCM-49 Catalyst and 2-Butene Feed

The process of Example 1 was repeated but with the MCM-22 catalyst replaced by 0.6 gm of MCM-49 catalyst (1/20" quadralobe extrudate with 60% MCM-49/40% Versal 200 alumina binder cut to 1/20" length). The catalyst was on stream for 4 days at 2.7 WHSV of butene with 97-98% butene conversion, 1 day at 8 WHSV with 97% conversion, 0.5 days at 12 WHSV with 93% conversion, 1.6 days at 2.7 WHSV with 98% conversion, 0.3 days at 19.2 WHSV with 86% conversion, and followed by 0.7 days at 2.7 WHSV with 98% conversion. Representative data are shown in Table 2.

TABLE 2

| sec-Butylbenzene Production with MCM-49 Catalysts and 2-Butene Feed | | | | | | |
|---|---|---|---|---|---|---|
| Days on Stream | 1.0 | 3.9 | 4.7 | 6.9 | 7.1 | 7.9 |
| Butene WHSV, $h^{-1}$ | 2.7 | 2.7 | 8.0 | 2.7 | 19.2 | 2.7 |
| 2-Butene Conv, % | 97.6 | 97.3 | 96.7 | 97.7 | 86.3 | 97.6 |
| Product Selectivity, wt % | | | | | | |
| Iso-Butane | 0.006 | 0.007 | 0.004 | 0.005 | 0.003 | 0.003 |
| Iso-Butene & 1-Butene | 0.000 | 0.000 | 0.000 | 0.000 | 0.358 | 0.000 |
| $C_5$-$C_7$ | 0.164 | 0.109 | 0.109 | 0.107 | 0.089 | 0.111 |
| $C_8$ and $C_{12}$ (butene oligomers) | 0.586 | 1.144 | 1.428 | 1.418 | 1.852 | 1.308 |
| Cumene | 0.054 | 0.057 | 0.045 | 0.060 | 0.042 | 0.043 |
| t-Butylbenzene | 0.125 | 0.128 | 0.069 | 0.105 | 0.042 | 0.091 |
| iso-Butylbenzene* | 0.000 | 0.000 | 0.000 | 0.000 | 0.000 | 0.000 |
| sec-Butylbenzene | 92.659 | 92.319 | 92.400 | 92.693 | 91.759 | 93.513 |
| n-Butylbenzene | 0.012 | 0.023 | 0.025 | 0.028 | 0.013 | 0.013 |
| Di-butylbenzene | 5.818 | 5.752 | 5.664 | 5.266 | 5.649 | 4.672 |
| Tri-butylbenzene | 0.513 | 0.425 | 0.250 | 0.304 | 0.189 | 0.241 |
| Heavies | 0.062 | 0.036 | 0.006 | 0.016 | 0.006 | 0.007 |
| Sum | 100.0 | 100.0 | 100.0 | 100.0 | 100.0 | 100.0 |
| Butylbenzene Composition % | | | | | | |
| t-Butylbenzene | 0.135 | 0.139 | 0.075 | 0.113 | 0.046 | 0.097 |
| iso-Butylbenzene* | 0.000 | 0.000 | 0.000 | 0.000 | 0.000 | 0.000 |
| sec-Butylbenzene | 99.852 | 99.836 | 99.898 | 99.857 | 99.940 | 99.889 |
| n-Butylbenzene | 0.013 | 0.025 | 0.027 | 0.030 | 0.014 | 0.014 |
| Sum | 100.0 | 100.0 | 100.0 | 100.0 | 100.0 | 100.0 |

All samples collected at 160° C., 300 psig, and 3:1 benzene/butene molar ratio.
*iso-Butylbenzene less than 0.5% in total butylbenzene not detectable with GC used.

Example 3

Sec-Butylbenzene Production with MCM-22 Catalyst and Raffinate-2 Type Feed

A 1.0 gram sample of an MCM-22 catalyst (65 wt % MCM-22/35% alumina binder) was used for the alkylation of benzene with Raffinate-2 type feed. This is the same catalyst used in Example 1. The Raffinate-2 type feed is a synthetic blend with the following composition: 53.4% cis-butene, 41.2% trans-butene, 4.6% isobutene, 0.5% butadiene, 0.1% n-butane and 0.2% others. The catalyst was in the form of a 1.6 mm (1/16") diameter cylindrical extrudate and was diluted with sand to 3 cc and loaded into an isothermal, down-flow, fixed-bed, tubular reactor having an outside diameter of 4.76 mm (3/16"). The catalyst was dried at 150° C. and 1 atm with 100 cc/min flowing nitrogen for 2 hours. The nitrogen was turned off and benzene was fed to the reactor at 60 cc/hr until reactor pressure reached the desired 300 psig (2170 kPa). Benzene flow was then reduced to 7.63 cc/hr (6.67 WHSV) and Raffinate-2 type feed was introduced from a syringe pump at 2.57 cc/hr (1.6 WHSV). The reactor temperature was adjusted to 160° C. Feed benzene/butene molar ratio was maintained at 3:1 for the entire run. Liquid product was collected in a cold-trap and analyzed off line. Butene conversion was determined by measuring unreacted butene relative to feed butene. The catalyst was on stream for 6 days at 1.6 WHSV of butene with 98% 2-butene conversion, 1 day at 4.8 WHSV with 80% conversion, 1 day at 7.2 WHSV with 62% conversion, and followed by 4 days again at 1.6 WHSV with 97% conversion. Representative data are shown in Table 3.

Example 4

Sec-Butylbenzene Production with MCM-49 Catalyst and Raffinate-2 Type Feed

The process of Example 3 was repeated but with the MCM-22 catalyst replaced by 0.5 gm of MCM-49 catalyst used in Example 2. The MCM-49 was on stream for 3 days at 3.2 WHSV of butene with 96% conversion, 1 day at 9.6 WHSV with 80-83% conversion, and 3 days at 3.2 WHSV with 95% conversion. Representative data are shown in Table 4.

TABLE 3 sec-Butylbenzene Production with MCM-22 and Raffinate-2 Type Feed

| Sample # | 1 | 3 | 6 | 8 | 11 | 13 | 15 |
|---|---|---|---|---|---|---|---|
| Days on Stream | 0.79 | 2.79 | 5.79 | 7.33 | 8.19 | 9.8 | 11.79 |
| Butene WHSV, h$^{-1}$ | 1.6 | 1.6 | 1.6 | 4.8 | 7.2 | 1.6 | 1.6 |
| 2-Butene Conv, % | 98.6 | 98.0 | 98.4 | 79.8 | 62.1 | 96.9 | 97.0 |
| Isobutene Conv, % | 98.2 | 96.3 | 96.8 | 64.4 | 35.8 | 93.7 | 94.0 |
| Butadiene Conv, % | 100.0 | 100.0 | 100.0 | 100.0 | 96.4 | 100.0 | 100.0 |
| Product Selectivity, wt % | | | | | | | |
| i-C$_4$ | 0.047 | 0.039 | 0.034 | 0.023 | 0.025 | 0.027 | 0.025 |
| C$_5$-C$_7$ | 0.388 | 0.525 | 0.467 | 0.541 | 0.640 | 0.556 | 0.555 |
| C$_8$ and C$_{12}$ (butene oligomers) | 8.739 | 7.886 | 7.746 | 10.343 | 12.852 | 7.916 | 8.230 |
| Cumene | 0.175 | 0.183 | 0.189 | 0.183 | 0.194 | 0.196 | 0.172 |
| t-Butylbenzene | 2.319 | 1.577 | 1.521 | 0.697 | 0.561 | 1.267 | 1.224 |
| iso-Butylbenzene* | 0.000 | 0.000 | 0.000 | 0.000 | 0.000 | 0.000 | 0.000 |
| sec-Butylbenzene | 81.330 | 83.058 | 83.282 | 82.789 | 81.265 | 83.453 | 83.406 |
| n-Butylbenzene | 0.034 | 0.059 | 0.055 | 0.063 | 0.058 | 0.060 | 0.062 |
| Di-butylbenzene | 5.227 | 5.559 | 5.580 | 4.642 | 3.972 | 5.465 | 5.312 |
| Tri-butylbenzene | 1.456 | 0.887 | 0.926 | 0.495 | 0.378 | 0.837 | 0.840 |
| Heavies | 0.284 | 0.225 | 0.200 | 0.225 | 0.055 | 0.224 | 0.174 |
| Sum | 100.0 | 100.0 | 100.0 | 100.0 | 100.0 | 100.0 | 100.0 |
| Butylbenzene Composition, % | | | | | | | |
| t-Butylbenzene | 2.772 | 1.863 | 1.792 | 0.835 | 0.685 | 1.494 | 1.445 |
| iso-Butylbenzene* | 0.000 | 0.000 | 0.000 | 0.000 | 0.000 | 0.000 | 0.000 |
| sec-Butylbenzene | 97.187 | 97.817 | 98.143 | 99.091 | 99.244 | 98.435 | 98.482 |
| n-Butylbenzene | 0.041 | 0.070 | 0.064 | 0.075 | 0.071 | 0.071 | 0.073 |
| Sum | 100.0 | 100.0 | 100.0 | 100.0 | 100.0 | 100.0 | 100.0 |

All samples collected at 160° C., 300 psig, and 3:1 benzene/butene molar ratio.

*iso-Butylbenzene less than 0.5% in total butylbenzene not detectable with GC used.

Table 3 shows that MCM-22 catalyst was effective for sec-butylbenzene production using a Raffinate-2 type feed. The 0.5% butadiene in butene feed had no significant effect on MCM-22 stability during the 12-day test cycle. The 4.6% isobutene in butene feed increased by-product formation. After initial lineout, selectivity measured at 97-98% 2-butene conversion was 8% for butene oligomers, 1.2-1.5% for t-butylbenzene, and 83% for sec-butylbenzene. This was a significant change when compared to results in Table 1 using the same catalyst and 2-butene feed. Selectivity measured with 2-butene feed at 97-98% 2-butene conversion was 1-2% for butene oligomers, 0.1-0.2% for t-butylbenzene, and 89-91% for sec-butylbenzene. The use of Raffinate-2 type feed resulted in a 50% activity drop for MCM-22.

Table 4 shows that MCM-49 catalyst was also effective for sec-butylbenzene production using a Raffinate-2 type feed. The 0.5% butadiene in the feed had no significant effect on MCM-49 stability during the 7-day test cycle. The 4.6% isobutene in butene feed increased by-product formation. Selectivity measured at 96% 2-butene conversion was 8% for butene oligomers, 1.2-1.8% for t-butylbenzene, and 83-85% for sec-butylbenzene. This is a significant change when compared to results in Table 2 using the same MCM-49 catalyst and 2-butene feed. Selectivity measured with 2-butene feed at 97% 2-butene conversion was 1.5% for butene oligomers, 0.1% for t-butylbenzene, and 92% for sec-butylbenzene. The use of Raffinate-2 type feed resulted in a 50% activity drop for MCM-49.

TABLE 4 sec-Butylbenzene Production with MCM-49 and Raffinate-2 Type Feed

| Sample # | 2 | 5 | 8 |
|---|---|---|---|
| Days on Stream | 2.3 | 3.2 | 5.3 |
| Butene WHSV, h$^{-1}$ | 3.2 | 9.6 | 3.2 |
| 2-Butene Conv, % | 96.1 | 83.0 | 95.5 |
| Isobutene Conv, % | 97.7 | 67.2 | 92.8 |
| Butadiene Conv, % | 100.0 | 100.0 | 100.0 |
| Product Selectivity, wt % | | | |
| i-C$_4$ | 0.041 | 0.032 | 0.028 |
| C$_5$-C$_7$ | 0.527 | 0.503 | 0.583 |
| C$_8$ and C$_{12}$ (butene oligomers) | 7.688 | 9.732 | 8.185 |
| Cumene | 0.128 | 0.144 | 0.127 |
| t-Butylbenzene | 1.849 | 0.849 | 1.240 |
| iso-Butylbenzene* | 0.000 | 0.008 | 0.012 |
| sec-Butylbenzene | 82.977 | 84.284 | 84.720 |
| n-Butylbenzene | 0.062 | 0.059 | 0.068 |
| Di-butylbenzene | 5.431 | 3.878 | 4.273 |
| Tri-butylbenzene | 1.079 | 0.429 | 0.629 |
| Heavies | 0.218 | 0.082 | 0.134 |
| Sum | 100.0 | 100.0 | 100.0 |
| Butylbenzene Composition, % | | | |
| t-Butylbenzene | 2.179 | 0.996 | 1.441 |
| iso-Butylbenzene* | 0.000 | 0.010 | 0.013 |
| sec-Butylbenzene | 97.749 | 98.925 | 98.467 |
| n-Butylbenzene | 0.073 | 0.069 | 0.078 |
| Sum | 100.0 | 100.0 | 100.0 |

All samples collected at 160° C., 300 psig, and 3:1 benzene/butene molar ratio.
*iso-Butylbenzene less than 0.5% in total butylbenzene not detectable with GC used.

Example 5

Higher Olefins Production with MCM-22 Catalyst and Raffinate-2 Type Feed

A 2.3 gram sample of the MCM-22 catalyst used in Examples 1 and 3 was used to oligomerize the same synthetic Raffinate-2 type feed used in Examples 3 and 4. The catalyst was diluted with sand to 5 cc and loaded into an isothermal, down-flow, fixed-bed, tubular reactor having an outside diameter of 4.76 mm (3/16"). The catalyst was dried at 150° C. and 1 atm with 100 cc/min flowing nitrogen for 2 hours. The nitrogen was turned off and the feed was introduced to the reactor at 60 cc/hr until reactor pressure reached the desired 300 psig (2170 kPa). Feed flow was reduced to 2.59 cc/hr (0.7 WHSV) and the reactor temperature was adjusted to 140° C. and kept at this temperature for the entire run. Liquid product was collected in a cold-trap and analyzed off line. Representative data are shown in Table 5.

TABLE 5

Higher Olefins Production with MCM-22 and Raffinate-2 Type Feed

| Sample # | 14 | 15 | 16 | 17 |
|---|---|---|---|---|
| Days on Stream | 14.79 | 15.79 | 16.79 | 17.79 |
| Butenes Conversion % | 79.61 | 76.03 | 76.46 | 76.75 |
| Product Selectivity, wt % | | | | |
| Lights (C3-) | 0.00 | 0.01 | 0.01 | 0.01 |
| i-C4 | 0.01 | 0.03 | 0.03 | 0.03 |
| n-C4 | 0.00 | 0.00 | 0.00 | 0.00 |
| C5-7 | 6.15 | 1.12 | 1.19 | 1.13 |
| C8= | 58.06 | 61.50 | 61.08 | 61.46 |
| C9-11 | 12.51 | 13.22 | 13.31 | 13.18 |
| C12= | 16.51 | 17.28 | 17.06 | 17.34 |
| C16= | 6.23 | 6.19 | 6.51 | 6.31 |
| C20= | 0.53 | 0.65 | 0.76 | 0.55 |
| C24+ | 0.01 | 0.00 | 0.06 | 0.01 |
| sum | 100.0 | 100.0 | 100.0 | 100.0 |

All samples collected at 140° C., 300 psig, and 0.7 WHSV.

Example 6

Oxidation of Sec-Butylbenzene

Figure 1:
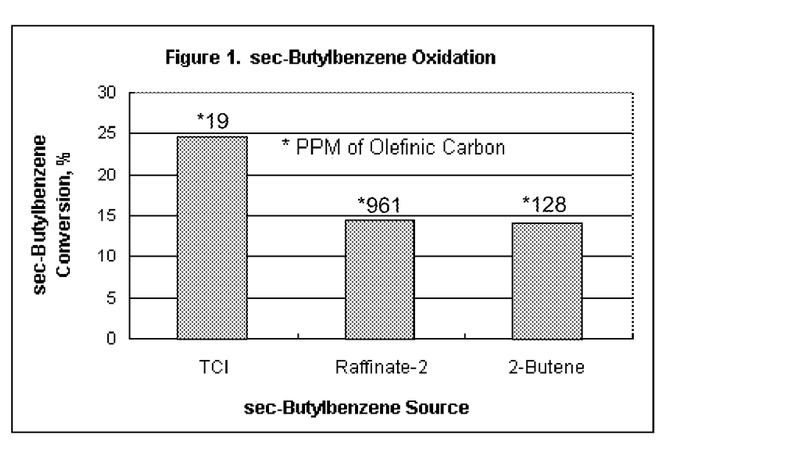
FIG. 1 is a chart comparing the degree of conversion obtained in the oxidation process of Example 6 using a commercially available sec-butylbenzene sample and using the sec-butylbenzene products of Examples 1, 2 (with 2-butene) and 3, 4 (with Raffinate-2).

To a 100 cc Parr autoclave equipped with a mechanical stirrer were charged 43.2 g (0.32 mole) of a substantially pure sec-butylbenzene supplied by TCI America and 0.185 g (0.001134 mole) of N-hydroxyphthalimide (NHPI, available from Aldrich). The autoclave was reassembled, leak tested with nitrogen then reattached to the system. The contents of the autoclave were pressurized with nitrogen followed by oxygen to obtain an 80:20 nitrogen/oxygen mixture at room temperature. The contents were then heated to 115° C. over a period of 6 hours, with the oxygen concentration being maintained at approximately 20% throughout the heating period by refilling with pure oxygen. Gas samples were taken throughout the heating period to test the oxygen concentration. This TCI sec-butylbenzene (with 19 ppm olefinic carbon as determined by $^{13}$C NMR) gave 24.5% conversion. The results are presented in FIG. 1.

The process was repeated with samples of sec-butylbenzene produced in Examples 1 and 2 (with 2-butene). This sec-butylbenzene (with 128 ppm olefinic carbon as determined by $^{13}$C NMR) gave 14% conversion. The results are also presented in FIG. 1. The process was also repeated with samples of sec-butylbenzene produced in Examples 3 and 4 (with Raffinate-2). This sec-butylbenzene (with 961 ppm olefinic carbon as determined by $^{13}$C NMR) gave 14.5% conversion. The results are also presented in FIG. 1. The results show that oxidation of sec-butylbenzene contaminated with higher olefin shows lower activity than TCI feed which has much less olefins.

Example 7

Figure 2:
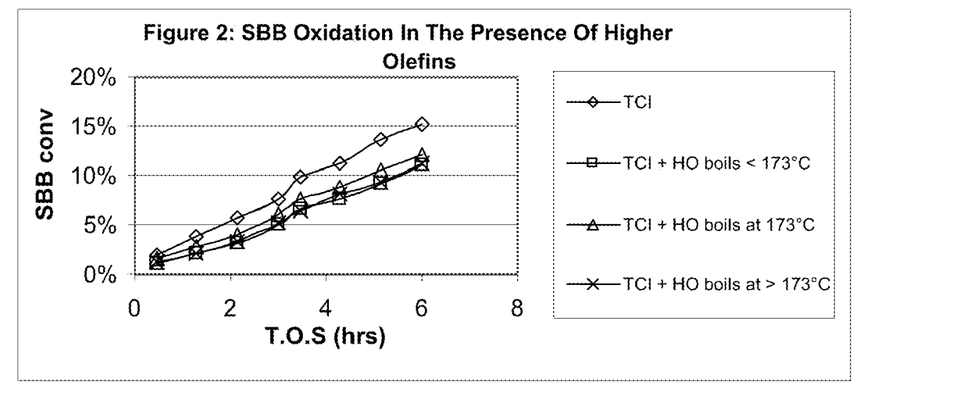
FIG. 2 is a graph comparing the degree of conversion obtained in the oxidation process of Example 7 using a commercially available sec-butylbenzene sample and using the same sample after spiking with various fractions produced by distillation of the butene oligomers obtained in Example 5.

Oxidation of Sec-Butylbenzene in the Presence of Higher Olefins,

To a 250-ml round bottom flask fitted with a condenser, stirrer and an air sparger, was charged 100 g of a substantially pure sec-butylbenzene supplied by TCI America and 0.375 g N-hydroxyphthalimide (NHPI, available from Aldrich). The flask was heated using a temperature-controlled heating mantle. The reaction temperature was 115° C. and the pressure was atmospheric. The air flow rate was approximately 220 cc/min. Every 45 minutes, a small aliquot of the reaction mixture was removed from the flask and analyzed by GC. The procedure was repeated, except the sec-butylbenzene feed was spiked with 1 gram samples of the higher olefin product obtained in Example 5. The higher olefin samples were obtained by diluting the reaction effluent with hexadecane and distilling the mixture under 50 mm Hg vacuum using a 26 plate vacuum jacketed Oldershaw column with a reflux ratio of 10 to 1. Three fractions were collected: i) a cut boiling at temperature before the sec-butylbenzene boiling point of 173° C., ii) a cut boiling in the same temperature region as sec-butylbenzene, and iii) a cut boiling at a temperature above the boiling point of sec-butylbenzene. The oxidation results are shown in FIG. 2 and Table 6. The results show that addition of olefins to sec-butylbenzene significantly reduced the rate of sec-butylbenzene oxidation.

TABLE 6

| sec-Butylbenzene (s-BB) Feed | Reaction rate %/hr |
|---|---|
| TCI s-BB | 2.5 |
| TCI s-BB + Higher Olefin (boils below 173° C.) | 2.0 |
| TCI s-BB + Higher Olefin (boils at 173° C.) | 1.83 |
| TCI s-BB + Higher Olefin (boils above 173° C.) | 1.86 |

Example 8

Removal of Higher Olefins from Sec-Butylbenzene by Acid Treatment

Into a 250 ml sample bottle equipped with a magnetic stirrer were added 94.9 grams (0.71 moles) sec-butyl benzene produced from a Raffinate-2 feed by the process of Examples 3 and 4 and 2.5 grams of sulfuric acid (97%). The mixture was stirred vigorously for 1 hour at room temperature. Next the sulfuric acid was removed by washing twice with 50 cc of distilled water. The upper sec-butyl benzene phase was then washed with 100 cc of a 5 wt. % sodium bicarbonate solution followed by 50 cc of distilled water. The sec-butylbenzene was then dried over 5A molecular sieve. A sample of the dried sec-butylbenzene was oxidized in a separate experiment as described under Example 5. The remaining sec-butylbenzene was distilled at 100 mm vacuum with a Claisson adapter at 98° C. and was then oxidized according to the procedure set out in Example 12.

Example 9

Removal of Higher Olefins from Sec-Butylbenzene by Hydrogenation

Into a 100 cc Parr autoclave were added sec-butyl benzene (47.5 g 0.354 mole) produced from a Raffinate-2 feed by the process of Examples 3 and 4 and 1.6 grams of palladium on alumina powder from Aldrich Chemical Co. The autoclave was reassembled, leak tested with nitrogen, then pressurized to 55 psig (480 kPa) with hydrogen. The hydrogen was vented and refilled to remove any nitrogen. The contents were heated with mechanical stirring to 100° C. and the temperature maintained at 100° C. for 3 hours. The hydrogen pressure in the autoclave was increased to and maintained at 60 psig throughout this heating period. The contents of the autoclave were then cooled to room temperature under a hydrogen atmosphere. At room temperature the reaction mixture was removed, filtered and oxidized in a separate experiment as described in Example 12.

Example 10

Removal of Higher Olefins from Sec-Butylbenzene by Acid Treatment and Hydrogenation Into a 100 cc Parr autoclave were added 55.4 grams (0.413 mole) sec-butyl benzene produced from a Raffinate-2 feed by the process of Examples 3 and 4, 5.0 grams of Amberlyst 35 from Rohm & Haas and 2.0 grams of 0.5% palladium on alumina ²⁰⁄₄₀ mesh. The mixture was then hydrogenated at 23-26° C., 57-61 psig (494–522 kPa) hydrogen pressure for 21 hours. The reaction mixture was then filtered, washed with 5% sodium bicarbonate followed by distilled water washing, dried over 5 Å molecular sieve then redistilled with a Claissen adapter at 97° C./80 mm vacuum. The distilled sec-butyl benzene was then oxidized according to the procedure set out in Example 12.

Example 11

Removal of Higher Olefins from Sec-Butylbenzene by Etherification

Into a 4-necked-200 ml round bottom flask equipped with a magnetic stirrer, thermometer, reflux condenser were added 63.3 grams (0.472 mole) sec-butyl benzene produced from a pure 2-butene feed by the process of Examples 1 and 2, 2.0 grams of Amberlyst 35 from Rohm & Haas and 3.5 grams (0.103 mole) methanol. The mixture was heated with stirring for 7 hours at 78-82° C. with methanol reflux. At the completion of the heating period, the reaction mixture was filtered and washed with 50 cc of a 5 wt. % sodium bicarbonate solution followed by 50 cc distilled water. The upper sec-butylbenzene was then dried over 5 Å molecular sieve and redistilled at 98° C./80 mm with a Claissen adapter. The distilled sec-butylbenzene was then oxidized according to the procedure set out in Example 12.

Example 12

Oxidation of Sec-Butylbenzene after Various Treatments

In this example the commercially available sec-butylbenzene from TCI America and samples of the treated sec-butylbenzene products from Examples 8 to 11 were separately oxidized according to the following procedure.

To a 100 cc Parr autoclave equipped with a mechanical stirrer were charged 43.2 g (0.32 mole) sec-butylbenzene and 0.185 g (0.001134 mole) NHPI. The autoclave was reassembled, leak tested with nitrogen then reattached to the system. The contents of the autoclave were pressurized with nitrogen followed by oxygen to obtain an 80:20 nitrogen/oxygen mixture at room temperature. The contents were then heated over a period of 6 hours to an operating temperature of 115° C. and the oxygen concentration was maintained at approx. 20% throughout the heating period by refilling with pure oxygen. Gas samples were taken throughout the heating period to maintain the oxygen concentration.

Figure 3:
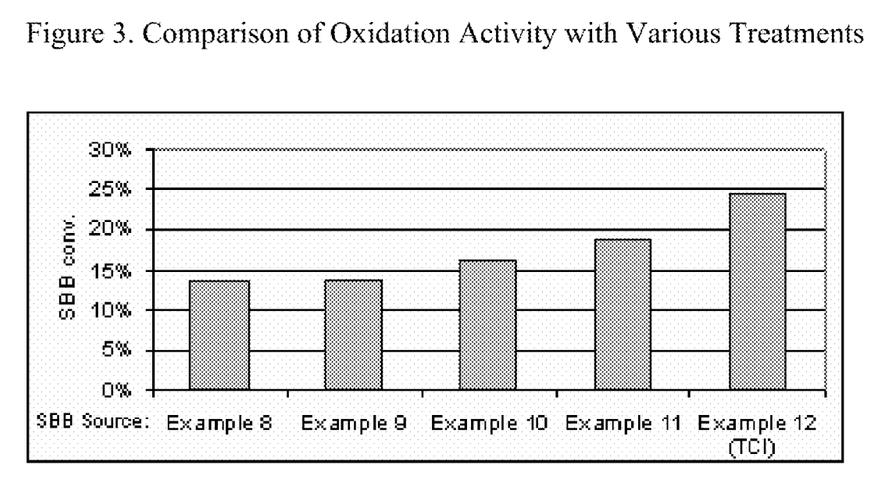
FIG. 3 is a chart comparing the degree of conversion obtained in the oxidation process of Example 12 using a commercially available sec-butylbenzene sample and using the untreated sec-butylbenzene product from Examples 1, 2 (with 2-butene) and 3, 4 (with Raffinate-2) and the treated sec-butylbenzene products from Examples 8 to 11.

The results are presented in FIG. 3. The results show any treatments which result in low olefin content improve the sec-butylbenzene oxidation rate.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A process for producing phenol and methyl ethyl ketone, the process comprising:

(a) contacting benzene and a C₄ olefin under alkylation conditions and in the presence of an alkylation catalyst to produce an alkylation effluent comprising sec-butylbenzene and butene oligomer, wherein said butene oligomer is a $C_8$ olefin or $C_{12}$ olefin;

(b) treating said effluent to reduce the amount of said butene oligomer and produce a treated effluent;

(c) oxidizing the sec-butylbenzene in said treated effluent to produce a hydroperoxide; and (d) cleaving the hydroperoxide from (c) to produce phenol and methyl ethyl ketone.

2. The process of claim 1, wherein the treating (b) includes at least one chemical treatment.

3. The process of claim 2, wherein said at least one chemical treatment is chosen from olefin oligomerization, selective reduction, selective oxidation, esterification, and etherfication, or a combination thereof.

4. The process of claim 2, wherein said at least one chemical treatment comprises an acid treatment wherein said effluent is contacted with at least one acid.

5. The process of claim 2, wherein said at least one chemical treatment comprises hydrogenation wherein said effluent is contacted with at least one acid to convert the butene oligomer to at least one of an alcohol and an ester.

6. The process of claim 2, wherein said at least one chemical treatment comprises hydrogenation wherein said effluent is contacted with hydrogen in the presence of a catalyst.

7. The process of claim 2, wherein said at least one chemical treatment comprises a combination of acid treatment wherein said effluent is contacted with at least one acid and hydrogenation wherein said effluent is contacted with hydrogen in the presence of a catalyst.

8. The process of claim 2, wherein said at least one chemical treatment comprises olefin oligomerization.

9. The process of claim 2 wherein said at least one chemical treatment comprises the addition of heteroatoms to olefins to make a product comprising an ether.

10. The process of claim 1, wherein the treating (b) reduces the amount of said butene-oligomer to less than 1 wt % of the treated effluent.

11. The process of claim 1, wherein the catalyst comprises at least one molecular sieve of the MCM-22 family.

12. The process of claim 11, wherein the molecular sieve of the MCM-22 family is selected from MCM-22, PSH-3, SSZ-25, ERB-1, ITQ-1, ITQ-2, MCM-36, MCM-49, MCM-56, UZM-8, and mixtures thereof.

13. The process of claim 1, wherein said $C_4$ olefin comprises a linear butene.

14. The process of claim 13, wherein said linear butene is contained in a mixed $C_4$ stream.

15. The process of claim 1, wherein said alkylation conditions include a temperature of from about 60° C. to about 260° C., a pressure of 7000 kPa or less, a feed weight hourly space velocity (WHSV) based on $C_4$ alkylating agent of from about 0.1 to about 50 $hr^{-1}$ and a molar ratio of benzene to butene from about 1 to about 50.

16. The process of claim 1, wherein said reacting is conducted under at least partial liquid phase conditions.

17. The process of claim 1, wherein said oxidizing (c) is conducted in the presence of a catalyst selected from:

(a) an oxo(hydroxo) bridged tetranuclear metal complex comprising manganese;

(b) an oxo(hydroxo) bridged tetranuclear metal complex having a mixed metal core, one metal of the core being a divalent metal selected from Zn, Cu, Fe, Co, Ni, Mn and mixtures thereof and another metal being a trivalent metal selected from In, Fe, Mn, Ga, Al and mixtures thereof;

(c) an N-hydroxy substituted cyclic imide either alone or in the presence of a free radical initiator; and (d) N,N',N"-trihydroxyisocyanuric acid either alone or in the presence of a free radical initiator.

18. The process of claim 1, wherein the oxidizing (c) is conducted at a temperature of about 70° C. to about 200° C. and a pressure of about 0.5 to about 20 atmospheres (50 to 2000 kPa).

19. The process of claim 1, wherein the cleaving (d) is conducted in the presence of a heterogeneous catalyst comprising a smectite clay.

20. The process of claim 1, wherein the cleaving (d) is conducted at a temperature of about 40° C. to about 120° C., a pressure of about 100 to about 1000 kPa, and a liquid hourly space velocity (LHSV) based on the hydroperoxide of about 1 to about 50 $hr^{-1}$.

* * * * *